(12) United States Patent
Short

(10) Patent No.: US 6,919,068 B2
(45) Date of Patent: Jul. 19, 2005

(54) METHOD OF PREPARING GAS-FILLED POLYMER MATRIX MICROPARTICLES USEFUL FOR ECHOGRAPHIC IMAGING

(75) Inventor: Robert E. Short, Los Gatos, CA (US)

(73) Assignee: Point Biomedical Corporation, San Carlos, CA (US)

( * ) Notice: Subject to any disclaimer, the term of this patent is extended or adjusted under 35 U.S.C. 154(b) by 235 days.

(21) Appl. No.: 10/150,449

(22) Filed: May 17, 2002

(65) Prior Publication Data

US 2003/0215393 A1 Nov. 20, 2003

(51) Int. Cl.[7] .............................. A61B 8/00; A61K 9/50; B01F 17/00
(52) U.S. Cl. ........................ 424/9.52; 424/501; 516/11; 516/77
(58) Field of Search ................................ 424/9.51, 9.52, 424/489, 490, 491, 492, 493, 494, 495, 496, 497, 498, 499, 500, 501, 450; 264/4.3; 516/11, 77

(56) References Cited

U.S. PATENT DOCUMENTS

| | | | |
|---|---|---|---|
| 5,102,983 A | 4/1992 | Kennedy | |
| 5,190,766 A | 3/1993 | Ishihara | |
| 5,558,082 A | 9/1996 | Spencer | |
| 5,580,575 A | 12/1996 | Unger et al. | |
| 5,711,933 A | * 1/1998 | Bichon et al. | ............. 424/9.52 |
| 6,045,777 A | 4/2000 | Church et al. | |
| 6,333,021 B1 | 12/2001 | Schneider et al. | |

FOREIGN PATENT DOCUMENTS

| | | | | |
|---|---|---|---|---|
| WO | WO 98/48783 | * | 11/1998 | ............ A61K/9/50 |

* cited by examiner

Primary Examiner—Michael Hartley
(74) Attorney, Agent, or Firm—Dechert LLP

(57) ABSTRACT

A method is provided to prepare gas-filled, porous microparticles having a polymer matrix interior which are useful as ultrasound echogenic contrast agents. An oil-in-water suspension is formed, both phases are frozen, then the aqueous and nonaqueous frozen phases are removed by sublimation. The resulting porous microparticles can receive a gas and be used as an ultrasound contrast agent.

16 Claims, 2 Drawing Sheets

METHOD OF PREPARING GAS-FILLED POLYMER MATRIX MICROPARTICLES USEFUL FOR ECHOGRAPHIC IMAGING

TECHNICAL FIELD

This invention pertains to a method of preparing gas-filled microparticles having a polymer matrix interior. Such microparticles are useful as a blood pool echogenic contrast agent for ultrasonic echography.

BACKGROUND

Ultrasound is a modem medical imaging modality using sound energy to noninvasively visualize the interior structures and organs of a patient. Pulses of high frequency sound, generally in the megaHertz (MHz) range, emitted from a hand-held transducer are propagated into the body where they encounter different surfaces and interfaces. A portion of the incident sound energy is reflected back to the transducer that converts the sound waves into electronic signals which are then presented as a two-dimensional echographic image on a display monitor.

One of the advances in ultrasound imaging has been the development of ultrasonic contrast agents. Use of contrast agents enables the sonographer to visualize the vascular system which is otherwise relatively difficult to image. In cardiology for example, ultrasound contrast injected into the bloodstream permits the cardiologist to better visualize heart wall motion with the opacification of the heart chambers. Perhaps more importantly, contrast can be used to assess perfusion of blood into the myocardium to determine the location and extent of damage caused by an infarct. Similarly, visualization of blood flow using ultrasound contrast in other organs such as the liver and kidneys has found utility in diagnosing disease states in these organs.

The first encapsulated contrast agent was developed by Tickner et al (Final Report NHLB1 Contract No. HR-62917-1A, National Institute of Health, 1977; U.S. Pat. No. 4,276,885), made of a gelatin membrane encapsulating a nitrogen bubble. The bubble diameter, while precise, was not small enough to circulate through the capillary beds and therefore was not appropriate for systemic delivery. An agent was later developed to include a lipophilic material in a saccharide composition to provide a microbubble of sufficient stability to enable pulmonary capillary transmission (Circulation 62 (Supp. III): III-34, 1980).

SUMMARY

This invention pertains to a novel method of preparing gas-filled polymer matrix microparticles suitable for use as an ultrasound contrast agent. The method of preparation comprises the steps of:

1. dissolving a polymer in a substantially water-immiscible solvent;

2. emulsifying the polymer solution in an aqueous medium, optionally containing suitable surfactants and bulking agents;

3. reducing the temperature of the emulsion wherein both aqueous and water-immiscible phases become frozen;

4. removing water from the aqueous and solvent from water-immiscible phase by means of sublimation, resulting in the formation of polymer matrix microparticles;

5. introducing a gas into the polymer matrix microparticles.

Step 2 may be modified such that the aqueous medium also contains a biologically compatible amphiphilic material which encapsulates the emulsion droplets. Upon crosslinking, the amphiphilic material becomes a contiguous outer layer of the microparticle.

The method may also include, after step 2, the step of replacing the aqueous medium with a second aqueous medium. This additional step is useful when the components of an aqueous medium optimized for emulsion of the polymer solution are different from the components of an aqueous medium optimized for lyophilization. The additional step may be achieved by centrifugation or by diafiltration.

Also provided is a method of ultrasound imaging of organs or tissue of a patient comprising the steps of:

1. injecting into a patient a suspension of gas-filled polymer matrix microparticles in a physiologically acceptable aqueous liquid carrier, where the microparticles have a mean size of about 1 to 10 microns and are made from a biodegradable synthetic polymer, and 2. echographically imaging the patient at an organ or tissue of interest.

DETAILED DESCRIPTION

Figure 1:
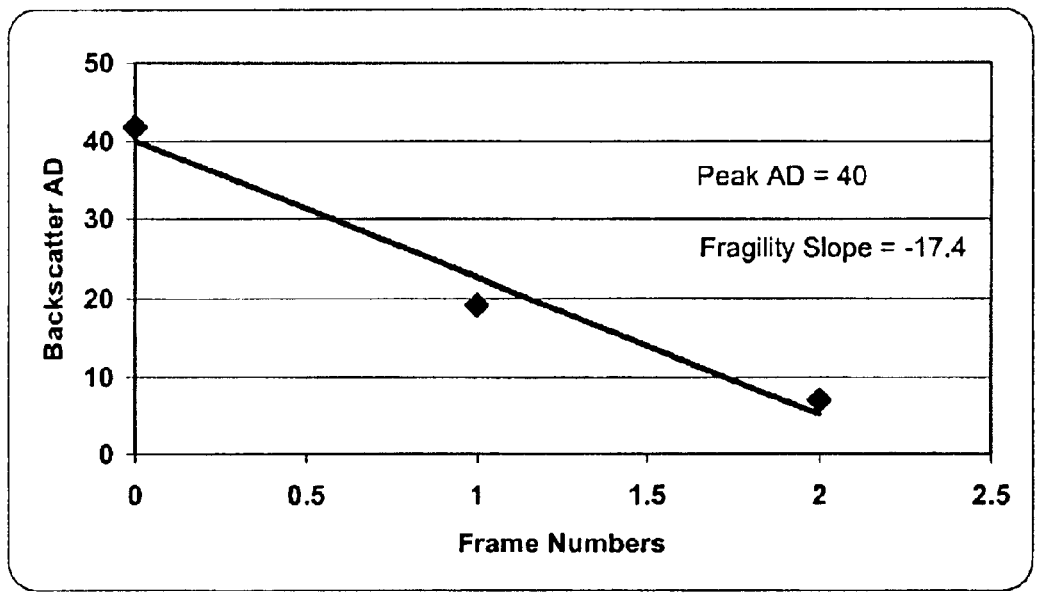
FIG. 1 is a plot of frame number vs. acoustic densitometry backscatter taken on an ultrasonic scanner as described in Example 3 for a test of the microparticles made in accordance with Example 1.

The present invention provides a method of manufacturing gas-filled porous microparticles having a polymer matrix interior. Such microparticles are useful as an ultrasonic contrast agent. These microparticles, being porous, rely on the hydrophobicity of the polymer to retain the gas within. The microparticles may be produced to also include an outer layer of a biologically compatible amphiphilic material, thus providing a surface for chemical modification to serve various purposes.

The process of manufacture utilizes a different emulsion solvent removal technique from those typically used to produce solid polymer microspheres. Typically, the solvent undergoing phase change is evaporated. According to the process of the present invention, solvent removal is effected by sublimation by lyophilization. In an evaporation process, mobile polymer molecules in the liquid phase will cohere to form a solid microsphere when solvent is removed. However, the initial freezing in lyophilization immobilizes the polymer molecules so that when solvent is removed under vacuum, a network of interstitial void spaces surrounded by a web-like polymer structure remains. This porous structure can then be filled with a gas.

The fabrication of the matrix microparticles starts with the preparation of the polymer and water-immiscible solvent solution. Preferred polymers are biodegradable synthetic polymers such as polylactide, polycaprolactone, polyhydroxyvalerate, polyhydroxybutyrate, polyglycolide and copolymers of two or more thereof. The requirements for the polymer solvent are that it is substantially water-immiscible and practicably lyophilizable. By practicably lyophilizable it is meant that the solvent freezes at a temperature well above the temperature of a typical lyophilizer minimum condensing capability and that the solvent will sublimate at reasonable rate in vacuo. Suitable solvents include p-xylene, cyclooctane, benzene, decane, undecane, cyclohexane and the like. Polylactide in xylene is a preferred solution.

The concentration of polymer in solution will dictate the void volume of the end product which, in turn, will impact acoustic performance. A high concentration provides lower void volume and a more durable microparticle. Acoustic modalities particularly relying on bubble breakage will exhibit performance variation depending on polymer concentration. Polymer molecular weight also has an effect. A low molecular weight polymer produces a more fragile particle. Optionally, additives may be used in the polymer organic phase. Plasticizers to modify elasticity of the polymer or other agents to affect hydrophobicity of the microparticle can be added to modify the mechanical, and thus acoustic, characteristics of the microparticle. Such plasticizers include the phthalates or ethyl citrates. Agents to modify hydrophobicity include fatty acids and waxes.

The polymer solution is then emulsified in an aqueous phase. The aqueous phase may contain a surface active component to enhance microdroplet formation and provide emulsion stability for the duration of the fabrication process. Surface active components include the poloxamers, tweens, brijs. Also suitable are soluble proteins such as gelatin, casein, albumin, or synthetic polymers such as polyvinyl alcohol.

Addition of viscosity enhancers may also be beneficial as an aid in stabilizing the emulsion. Useful viscosity enhancers include carboxymethyl cellulose, dextran, methyl cellulose, hydroxyethyl cellulose, polyvinyl pyrrolidone, and various natural gums such as gum arabic, carrageenan, and guar gum.

The range of ratios of the organic phase to the aqueous phase is typically between 2:1 and 1:20 with a 2:1 to 1:3 ratio range preferred.

If the aqueous phase is also to serve as the suspending medium during the lyophilization step, other components which may be included in the aqueous phase are ingredients suitable as bulking agents such as polyethylene glycol, polyvinyl pyrrolidone, sugars such as glucose, sucrose, lactose, and mannitol. Salts such as sodium phosphate, sodium chloride or potassium chloride may also be included to accommodate tonicity and pH requirements.

A variety of equipment may be used to perform the emulsification step including colloid mills, rotor-stator homogenizers, ultrasonic homogenizers, high pressure homogenizers, microporous membrane homogenizers, with microporous membrane homogenization preferred because the more uniform shearing provides for a more monodisperse population of emulsion droplets.

Size of the droplets formed should be in a range that is consistent with the application. For example, if the microparticles are to be injected intravenously, then they should have diameters of less than 10 microns in order to pass unimpeded through the capillary network. The size control can be empirically determined by calibration on the emulsification equipment.

If it is desired to provide an optional outer layer of a biologically compatible material, the material is first solubilized in the aqueous phase. This outer layer material will typically be amphiphilic, that is, have both-hydrophobic and hydrophilic characteristics. Such materials have surfactant properties and thus tend to be deposited and adhere to interfaces such as the outer surface of the emulsion droplets. Preferred materials are proteins such as collagen, gelatin, casein, serum albumin, or globulins. Human serum albumin is particularly preferred for its blood compatibility. Synthetic polymers may also be used such as polyvinyl alcohol.

The deposited layer of amphiphilic material can be further stabilized by chemical crosslinking. If proteinaceous, suitable crosslinkers include the aldehydes like formaldehyde and glutaraldehyde or the carbodiimides such as dimethylaminopropyl ethylcarbodiimide hydrochloride. To crosslink polyvinyl alcohol, sodium tetraborate may be used.

Provision for the outer layer is preferably achieved by diluting the prepared emulsion into an aqueous bath containing the dissolved crosslinker. This outer crosslinked layer also has the advantage of increasing the stability of the emulsion droplets during the later processing steps.

Provision of a separate outer layer also allows for charge and chemical modification of the surface of the microparticles without being limited by the chemical or physical properties of material present inside the microparticles. Surface charge can be selected, for example, by providing an outer layer of a type A gelatin having an isoelectric point above physiological pH or by using a type B gelatin having an isoelectric point below physiological pH. The outer surface may also be chemically modified to enhance biocompatibility, such as by pegylation, succinylation, or amidation, as well as being chemically binding to the surface targeting moiety for binding to selected tissues. The targeting moieties may be antibodies, cell receptors, lectins, selectins, integrins, or chemical structures or analogues of the receptor targets of such materials.

Optionally prior to lyophilization the outer aqueous phase may be replaced by a second aqueous phase. This would allow the first aqueous phase to be optimized for emulsification, then replaced by a second aqueous phase optimized for lyophilization. Replacement may be achieved by means of diafiltration or by centrifugation.

The emulsion is then lyophilized. This involves first freezing both the water immiscible organic phase in the emulsion droplets and the suspending aqueous phase, then removing both phases by sublimation in vacuo. The process produces a dry cake containing porous polymer matrix microparticles.

The microparticles are porous and thus can receive a gas. Introducing a selected gas into the lyophilization chamber after the drying step will fill the interstitial voids within the microparticle matrix interior. Alternatively, a selected gas can be exchanged for the gas used to repressurize the lyophilization chamber.

Any gas may be used, but biologically inert gases such as air, nitrogen, helium, oxygen, xenon, argon, helium, carbon dioxide, and halogenated hydrocarbons such as perfluorobutane, perfluoropropane or sulfur halides such as sulphur hexafluoride are preferred. Depending upon the application, one may select the gas based on its solubility in blood. For example, perfluorocarbons have low solubility while carbon dioxide has very high solubility. Such differences in solubility will influence the acoustic performance of the microparticle.

The dry cake can be reconstituted in an aqueous medium to form a suspension of gas-filled microparticles. The microparticle suspension when injected into the bloodstream, tissue, or cavity serves as a contrast agent for ultrasound. Typical applications for which the present invention can be used include visualization of myocardial perfusion, quantification of renal function, and delineation of tumor vascularization.

The following examples are provided by way of illustration and are not intended to limit the invention in any way.

EXAMPLE 1

Fabrication of Gas-filled Microparticle Having a Polymer Matrix Interior

An aqueous solution of 1% poly (vinyl alcohol) and 2.8% mannitol was prepared. Separately, a polymer solution containing 6% poly(DL-lactide) in p-xylene was prepared. To 40.0 g of the polymer solution was combined 50.0 g of the aqueous solution in a jacketed beaker maintained at 30° C. The mixture was then emulsified to create an oil-in-water emulsion using a circulating system consisting of a peristaltic pump and a sintered metal filter having a nominal pore size of 7 microns. After circulating for 6 minutes, 35.0 g of the resultant emulsion was diluted with 177.9 g of a 2.8% mannitol solution also maintained at 30° C. After 15 minutes of continuous stirring, a portion of the diluted emulsion was aliquoted into 10 ml vials and then lyophilized. After the drying cycle was complete, nitrogen gas was introduced into the lyophilization chamber to a pressure slightly below atmospheric and the vials stoppered.

Microscopic inspection of the reconstituted product revealed discrete gas-filled microparticles.

EXAMPLE 2

Fabrication of Gas-filled Microparticle Having a Polymer Matrix Interior and Comprising an Outer Layer A solution of 5.4% human serum albumin (hsa) was prepared by dilution of a 25% solution and the pH adjusted to 4 with HCl. Separately, 0.99 gm poly(D-L lactide) was dissolved in 29.0 gm p-xylene. In a jacketed beaker maintained at 40° C., the resulting polylactide solution was combined with 30 gms of the previously prepared hsa solution and a coarse emulsion was formed using magnetic stirring. A peristaltic pump was used to pump the coarse emulsion through a porous sintered metal filter element with a 2 μm nominal pore size. The emulsion was recirculated through the element for approximately 15 minutes until the average droplet size was less than 10 microns. The emulsion was diluted into 350 ml of a 40° C. aqueous bath containing 1.0 ml of a 25% glutaraldehyde solution and 1.4 ml of IN NaOH. After 15 minutes, 0.75 gm of poloxamer 188 surfactant was dissolved into the aqueous bath. The emulsion microdroplets were retrieved by centrifugation at 2000 rpm for 10 minutes, formulated into an aqueous solution containing polyethylene glycol, glycine, and poloxamer 188, aliquoted into 10 ml vials, and then lyophilized. After the drying cycle was completed, nitrogen gas was introduced into the lyophilization chamber to a pressure slightly less than atmospheric and the vials were stoppered.

Microscopic inspection of the reconstituted product revealed discrete gas-filled microparticles.

EXAMPLE 3

Contrast Efficacy of Gas-filled Microparticles Having a Polymer Matrix Interior An Agilent 5500 ultrasonic scanner was used for this study to measure the acoustic backscatter and fragility from a suspended matrix particle. This scanner has the capability of measuring the acoustic density (AD) as a function of time within a region of interest (ROI) displayed on the video monitor. The scanner was set to the 2D harmonic mode with send frequency of 1.8 MHz and receive frequency of 3.6 MHz. The test cell was a 2 cm diameter tube running the length of a Doppler flow phantom manufactured by ATL Laboratories of Bridgeport, Conn. Microparticle agent made in accordance with Example 1 was first reconstituted with deionized water. The resulting suspension was diluted into a 1 liter beaker containing water and then circulated through flow phantom using a peristaltic pump (Masterflex L/S manufactured by Cole-Parmer). To insure that the agent remained uniformly suspended in the beaker, mixing using a VWR Dylastir magnetic stirrer in conjunction with a 2 cm coated plastic stir bar was maintained throughout the duration of the testing. When data was to be collected, the pump was turned off resulting in no flow within the phantom.

The scanner transducer (s4 probe) was placed directly over the flow phantom within a water-well designed into the phantom. It was oriented 90 degrees to the flow axis such that the image of the flow tube on the monitor was circular. The ROI (21×21) was positioned by the operator within the image of the tubing lumen to be at the top center about 1 mm away from the top wall and free of any bright echoes caused by the wall. The scanner was set to the acoustic densitometry (AD) mode. This mode permits the scanner to read the mean densitometry within the ROI as a function of time using a triggered mode. The triggering interval was selected to be 200 milliseconds. For each test run, suspended agent was circulated into the flow tube and then flow was discontinued. Using a triggering interval of 200 milliseconds, the sample was then insonated and the acoustic densitometry within the ROI was measured at each frame. The tests were repeated at several scanner power levels.

Figure 2:
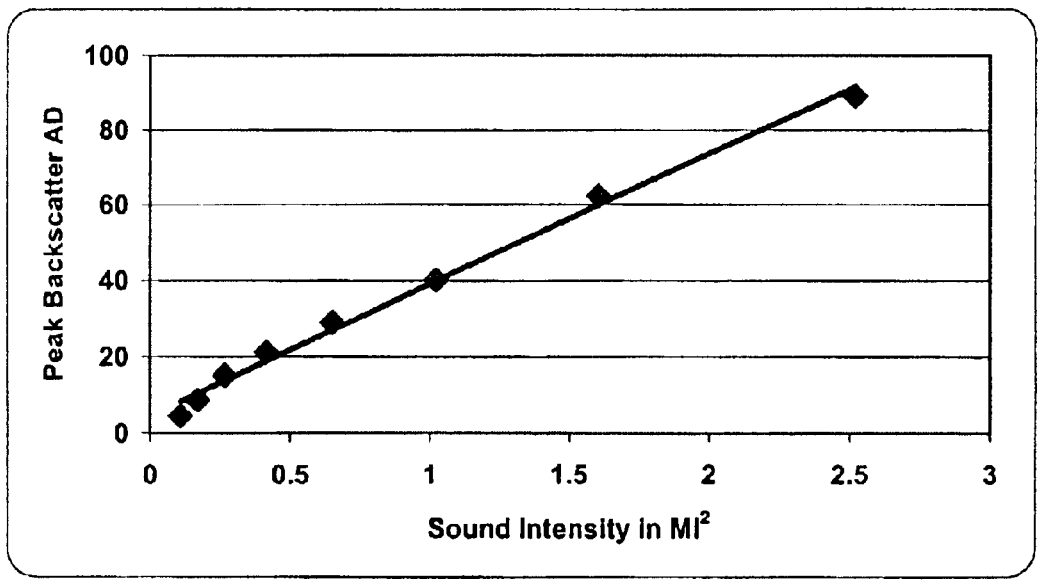
FIG. 2 is a plot of sound intensity in $MI^2$ vs. peak backscatter as described in Example 3.
Figure 3:
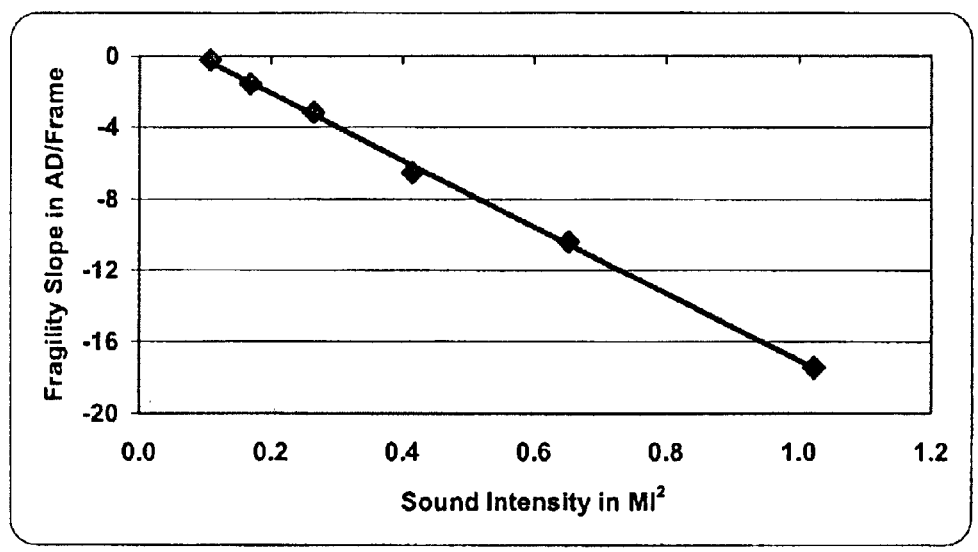
FIG. 3 is a plot of sound intensity in $MI^2$ vs. fragility slope as described in Example 3.

From the AD decay curve at each power setting, a linear regression curve was fit through the first three or four data points. The zero time intercept provides the peak backscatter produced by the agent as seen in FIG. 1. The slope of that curve is identified as the fragility slope and is a measure of the fragility of the agent. These two measurements are plotted respectively against intensity in FIGS. 2 and 3. Note that the backscatter of the matrix microparticle increases linearly with ultrasound intensity (FIG. 2) and this is considered typical behavior. The plot of fragility slope (FIG. 3) provides some additional information regarding the agent. First, it indicates that the agent is breaking. Secondly, its intercept with the x-axis in FIG. 3 identifies the point where it begins to break. Thus for this agent, at fragiligy slope −17.4 the agent begins to fail at an $MI^2$ value of intensity of 0.0868, which is a value of MI of 0.295. Thus for values of MI less than 0.295, the agent will not fail and therefore if drug were encapsulated within it would not be released.

What is claimed is:

1. A method of preparing gas-filled polymer matrix microparticles useful for echographic imaging, comprising the steps of:

a. emulsifying a polymer solution in an aqueous solution to form an oil-in-water emulsion-in which the polymer solution constitutes a discontinuous phase and the aqueous solution constitutes a continuous phase, wherein the polymer solution comprises a polymer dissolved in an organic solvent system that is substantially inmiscible with water;

b. freezing the oil-in-water emulsion;

c. removing the water and organic solvent system from the frozen emulsion by sublimation, thereby forming porous polymer matrix microparticles; and d. introducing a gas into the pores of the porous matrix microparticles.

2. A method according to claim 1, wherein said aqueous solution contains a biologically compatible amphiphilic material and the method further comprises the step subsequent to step a of diluting said emulsion into a second aqueous solution containing a chemical crosslinking agent, thereby forming an outer layer of crosslinked biologically amphiphilic material around said droplets.

3. A method according to claim 1 further comprising the step subsequent to step a of exchanging or partially exchanging said continuous phase by a second aqueous solution.

4. A method according to claim 1 wherein said polymer comprises a biodegradable synthetic polymer.

5. A method according to claim 4 wherein said biodegradable synthetic polymer is selected from the group consisting of polylactide, polycaprolactone, polyglycolide, polyhydroxybutyrate, polyhydroxyvalerate, and copolymers of any two or more thereof.

6. A method according to claim 5 wherein said biodegradable synthetic polymer is polylactide.

7. A method according to claim 2 wherein said biologically compatible amphiphilic material comprises a protein.

8. A method according to claim 7 wherein said protein is selected from the group consisting of serum albumin, gelatin, collagen, globulins, casein, and combinations of two or more thereof.

9. A method according to claim 8 wherein said protein is serum albumin.

10. A method according to claim 2 wherein said crosslinking agent comprises glutaraldehyde.

11. A method according to claim 1 wherein said water-immiscible solvent is selected from the group consisting of xylene, benzene, cyclohexane, cyclooctane, and combinations of two or more thereof.

12. A method according to claim 11 wherein said water-immiscible solvent is xylene.

13. A method according to claim 1 wherein said gas is selected from the group consisting of air, nitrogen, oxygen, argon, helium, carbon dioxide, xenon, a sulfur halide, and a halogenated hydrocarbon.

14. A method according to claim 13 wherein said gas is nitrogen.

15. A method of ultrasound imaging of organs or tissue of a patient, comprising the steps of:
   a. reconstituting microparticles having a mean size range of about 1 to about 10 microns prepared according to any one of claims 1 through 14 in a physiologically acceptable aqueous liquid carrier to form a microparticle suspension,
   b. injecting said suspension into said patient, and
   c. echographically imaging said patient at an organ or tissue of interest.

16. The method according to claim 15 wherein said microparticles comprise a biodegradable synthetic polymer.

* * * * *